United States Patent [19]

Zornes

[11] 4,269,789
[45] May 26, 1981

[54] PETROLEUM SULFONATION

[75] Inventor: David R. Zornes, Bartlesville, Okla.

[73] Assignee: Phillips Petroleum Company, Bartlesville, Okla.

[21] Appl. No.: 108,303

[22] Filed: Dec. 31, 1979

[51] Int. Cl.³ .......................................... C07C 143/24
[52] U.S. Cl. ................................................ 260/505 P
[58] Field of Search ................................... 260/505 P

[56] References Cited

U.S. PATENT DOCUMENTS

| | | | |
|---|---|---|---|
| 2,655,530 | 10/1953 | Nevison | 260/505 P |
| 2,822,384 | 2/1958 | Gragson | 260/504 |
| 2,880,173 | 3/1959 | Honeycutt | 260/505 P |
| 3,007,868 | 11/1961 | Eck et al. | 252/33 |
| 3,374,210 | 3/1968 | Muller et al. | 260/79.3 |
| 3,798,261 | 3/1974 | Kemp | 260/504 R |
| 3,836,484 | 9/1974 | Danzik et al. | 252/550 |
| 3,888,917 | 6/1975 | Fentress et al. | 260/504 R |
| 3,910,994 | 10/1975 | Bloch et al. | 260/505 A |
| 3,956,372 | 5/1976 | Coleman et al. | 260/505 P |

*Primary Examiner*—Alan Siegel

[57] ABSTRACT

By contacting the petroleum sulfonate-containing reaction mixture of a sulfonation reaction with a lower alkane, a lower alkanol and water a more efficient separation of unreacted oil and petroleum sulfonate is possible.

9 Claims, No Drawings

PETROLEUM SULFONATION

This invention relates to a process to produce petroleum sulfonates. In another aspect, this invention relates to the separation of a reaction mixture containing petroleum sulfonates.

BACKGROUND

Petroleum sulfonates are representative anionic surfactants which carry one or more sulfonate groups per molecule of sulfonated hydrocarbon. These petroleum sulfonates are useful in a variety of applications such as surfactant flooding in post-primary oil recovery operations. Increasingly important is the use of petroleum sulfonates for oil recovery. Some of the petroleum sulfonates can be used in micellar solutions having essentially zero interfacial tension with the oil to be recovered.

It is known to produce petroleum sulfonates by contacting a petroleum fraction with a sulfonating agent. A diluent may be present during this reaction. The reaction product comprises petroleum sulfonic acids, unreacted starting materials and diluent. The sulfonic acid moieties are normally neutralized to form the petroleum sulfonate and the diluent (when used) is removed.

A problem in the recovery of the petroleum sulfonates is the separation thereof from a reaction mass containing several other hydrophilic and oleophilic materials. It has been proposed in the art to achieve this separation by extracting the petroleum sulfonate containing mixture with an aqueous alcohol such as isopropanol.

STATEMENT OF THE INVENTION

In accordance with this invention, it has been found that an excellent separation of the petroleum sulfonates and an efficient recovery of unreacted oil is possible by simultaneously contacting the petroleum sulfonate-containing mixture with a lower molecular weight hydrocarbon, a lower molecular weight alkanol and water. The recovery of petroleum sulfonates in accordance with this invention is significantly improved over a comparable process in which an alcohol/water mixture is used as the separating agent. One major advantage achieved by the process of this invention is that the phase separation can be carried out at room temperature.

It is thus one object of this invention to provide an efficient process for the production of petroleum sulfonates.

A further object of this invention is to efficiently separate a petroleum sulfonate from a mixture containing petroleum sulfonates, water, oil and salts.

Yet another object of this invention is to provide a process for the separation of a petroleum sulfonate from the reaction mixture utilizing relatively harmless chemicals which can be easily recovered and recycled and which when remaining associated with the various compounds will neither interfere with their reaction nor cause particular hazards in the process.

These and other objects, advantages, details, features and embodiments of this invention will become apparent to those skilled in the art from the following detailed description of the invention and the appended claims.

One embodiment of this invention resides in a process for producing petroleum sulfonates which comprises sulfonating a hydrocarbon oil feed stock, neutralizing the sulfonated product obtained, contacting the neutralized product obtained with a separating agent comprising a lower molecular weight alkane hydrocarbon, an alcohol and water to form a separation mixture, letting said mixture separate into a top phase, an intermediate phase and a bottom phase, and recovering said petroleum sulfonates from the intermediate phase.

In accordance with another embodiment of this invention, the sulfonating step is carried out in the presence of a halohydrocarbon diluent which is removed prior to the contacting of the neutralized product with the separating agent defined.

The petroleum fraction or oil that can be used in the process of this invention is a sulfonatable hydrocarbon feedstock. Examples for such feedstocks are vacuum gas oils and topped crude oils. Typical feedstocks are sulfonatable heavy petroleum fractions from a midcontinent crude. The vacuum gas oils can be those boiling in the range of 685° to 1145° F. (363°–618° C.). Typical topped crude oils that can be used for the purposes of this invention have a boiling range of 650°–1200° F. (343°–649° C.). Similar heavy fractions which have been refined for instance by solvent extraction can also be used. The preferred petroleum fractions to be used as feedstocks in this invention are oils such as vacuum gas oils having 15 to 50 weight percent aromatic compounds as well as topped crude oils having 10 to 40 weight percent aromatic compounds.

In the examples, a vacuum gas oil feedstock boiling in the range of 685°–1145° F. (363°–618° C.) with average molecular weights of about 424 (vapor phase osmometry) was used. The boiling range of an oil is defined by two temperatures, namely a lower temperature at which 5 percent of the oil has been distilled off and a higher temperature at which 95 percent of the oil has been distilled off. Other properties of such a typical vacuum gas oil are as follows: Refractive index at 70° C.: 1.4987; API gravity at 60° F.: 30.4; pour point 105° F.; and viscosity 65.3 SUS (at 210° F.). Also used was a topped crude oil feedstock boiling in the range of 650°–1200° F. (343°–649° C.) with average molecular weight of about 463 (vapor phase osmometry). Other properties of such a typical topped crude oil are as follows: Refractive index at 70° C.: 1.4896; API gravity at 60° F.: 23.8; pour point 30° F.; and viscosity 18.5 SUS (at 210° F.). Mass spectral analyses showed, respectively, 33.1 and 18.0 weight percent aromatic compounds in a typical vacuum gas oil and a typical topped crude oil.

The sulfonation step can be carried out using any suitable sulfonation process. Thus, the feedstock can be contacted with $SO_3$ in a suitable diluent, such as methylene chloride, at temperatures in the range of 50°–200° F. (10°–93° C.), preferably 85°–110° F. (29°–43° C.). About 0.025°–0.20, preferably 0.05–0.15 lb of $SO_3$ per lb feedstock can be used.

In the examples, sulfonations of the above-described feedstocks were carried out in boiling methylene chloride as a diluent at a reaction temperature of 95°–102° F. (35°–39° C.). Sulfur trioxide treat rates of about 0.1 lb $SO_3$ per pound of feedstock were usually employed.

Following the sulfonation the reaction mass is neutralized. Any conventionally employed neutralization method (such as neutralization with an alkali metal base) can be used. Generally, the sulfonic acids in the reaction mass are neutralized to a pH in the range of 8 to 9. The neutralizing agent can, for instance, be sodium hydroxide, preferably in an aqueous solution containing 10 to 20 weight percent sodium hydroxide.

Prior to or following the neutralization step, the diluent when utilized is removed from the neutralized reaction product. In the case of methylene chloride used as a diluent this removal can be done under reduced pressure. Generally, the removal of the diluent is carried out prior to the new separation or work-up step to be described in the following.

In accordance with this invention, in the sulfur trioxide sulfonation process which involves the steps of sulfonation, neutralization, distillation, and separation, a significant improvement is achieved by utilizing an improved product recovery procedure involving the addition of aqueous alcohol and volatile alkane hydrocarbon. The separating agent which contains as the main ingredient an alkane hydrocarbon, an alcohol and water is added to the neutralized sulfonation reaction mixture after the removal of any diluent. Thereby the separation or resolution of the product mixture into three phases comprising an aqueous alcohol phase, an alkane oil phase and a brine phase is facilitated. The alkane oil phase contains unsulfonated oil as well as alkane from the separating agent. The alcohol phase contains alcohol, water, and the desired petroleum sulfonate which will be sodium petroleum sulfonate if sodium hydroxide has been used for the neutralization step. The brine phase contains water, some inorganic salts and sludge.

Utilizing the preferred combination of pentane, isopropyl alcohol and water as the separating agent and, for instance, sodium hydroxide as the neutralizing agent, the treatment of the residual liquid comprising sodium petroleum sulfonates and unsulfonated oil with the described inventive work-up procedure will result in three liquid phases namely one liquid phase comprising unsulfonated oil and pentane, one liquid phase comprising sodium petroleum sulfonates in aqueous isopropanol and one liquid phase comprising predominantly sodium sulfate in water.

According to the present invention, the volume ratio of alkane:alcohol:water varies over the broad range of 6:6:1 to 0.25:2:3 with a preferred range of 4:4:1 to 0.5:1:1. The amount of water used varies from 0.25 ml to 2 ml per gram of feedstock. The optimum amounts of these solvents will depend on the specific petroleum fractions used, their crude source, and the degree of sulfonation. However, routine experimentation can determine the proportions which result in the optimum resolution of a given mixture into three liquid phases which are convenient, economical and easily separable.

In addition to n-pentane, other suitable alkane hydrocarbons include compounds containing five to ten carbon atoms such as isopentane, hexane, heptane, octane, nonane and decane. It is also contemplated that selected cyclic alkane hydrocarbons such as cyclopentane and cyclohexane can also be used in the inventive procedure.

In addition to isopropanol other suitable alcohols include alkanols containing one to four carbon atoms such as methanol, ethanol, n-propanol, isobutyl alcohol, sec-butyl alcohol and the like, and mixtures thereof.

After sulfonation, neutralization, and sulfonation diluent removal, the crude product is thoroughly mixed with the appropriate amounts of alkane, alkanol and water using any suitable mixing device. The mixture is then allowed to settle into the three liquid phases with the desired sulfonate being predominantly concentrated in the alkanolic middle phase. The isolation and recovery of the sulfonate can then be completed by removal of the alkanol and volatiles by any suitable method such as stripping.

The inventive work-up procedure is carried out at ambient conditions of temperature and pressure. The phase separation step is preferably carried out at ambient temperature in the range of 10° to 40° C.

In accordance with the instant teaching, separation of unsulfonated oil, inorganic salts and the sodium petroleum sulfonates is effected by the addition of hydrocarbon diluent, alcohol and water resulting in the appearance of three distinct phases consisting essentially of a hydrocarbon diluent/unsulfonated oil upper phase, a middle aqueous alcohol/sodium petroleum sulfonate phase and a bottom aqueous sodium sulfate phase. Flashing of the upper and middle phases provides, respectively, hydrocarbon diluent and alcohol for recycle.

Residual material from the stripped middle phase is suitable for use as surfactant in an enhanced oil recovery operation. However, if desired, the sodium petroleum sulfonates contaminated with a small amount of unsulfonated oil can be further purified, e.g., by elution column chromatography as is well known in the art. Sulfate ashing technique (ASTM D855-56) can be used for equivalent weight determination on the thus isolated sodium petroleum sulfonates.

EXAMPLE I

A 300 g sample of vacuum gas oil containing 33.1 weight percent aromatic compounds and 2500 ml of methylene chloride was charged to a 5-liter 3-necked round-bottomed flask equipped with a Y-adapter tube, water-cooled reflux condenser, thermometer, air-powered stirrer, and glass tubing for the introduction of sulfur trioxide. A 25 ml graduated cylinder with inlet and outlet tubes, respectively, for introduction of nitrogen and entrainment of a $N_2/SO_3$ stream was used as a liquid $SO_3$ reservoir which was connected to the reaction vessel by glass tubing such that the entire system was maintained anhydrous under a nitrogen atmosphere. A nitrogen bubbler atop the reflux condenser was used to monitor the flow rate of nitrogen through the sulfonation system. A manually operated heat gun was used to regulate vaporization and entrainment of the liquid $SO_3$ from the reservoir into the reaction vessel.

Approximately 15 ml (28.8 g, 0.36 mol) of $SO_3$ was vapor-transferred into the stirred reaction mixture of $CH_2Cl_2$ and vacuum gas oil over a period of 3.25 hours and the resulting mixture was stirred an additional hour after all of the $SO_3$ had been added. The reaction mass was treated with approximately 149.5 ml of 10 weight percent aqueous sodium hydroxide solution to neutralize the sulfonic acids and adjust the pH into the range of 8-9. Methylene chloride was stripped at reduced pressure and to the residual material was added at room temperature 300 ml of pentane, 600 ml isopropanol and 150 ml water to give rise to three distinct phases (Volume Ratio 2:4:1 for pentane:isopropanol:water; 0.5 ml $H_2O$/g feedstock). The phase separation occurring at room temperature is an important advantage of the process of this invention.

The separated top phase was stripped of pentane leaving a residue of about 214 g of unsulfonated oil which corresponds to about 71.4 weight percent of the 300 g of vacuum gas oil charged to the reactor.

After stripping the middle phase on a rotary evaporator to remove most of the isopropanol, a fluid residue of 181.86 g was obtained. A 20 g sample of this phase was subjected to an azeotropic distillation with toluene to give 7.5 ml water (37.5 weight percent $H_2O$). A 20 g sample of the remaining organic phase was taken into chloroform and characterized by silica gel elution column chromatography to establish the presence of 2.62 g of unsulfonated oil (13.1%) and 9.56 g of sodium petroleum sulfonates (47.6%). Thus, the principal components in the 181.86 g stripped middle phase were sodium petroleum sulfonates 86.4 g (47.6%), water 68.2 g (37.5%) and unsulfonated oil 23.8 g (13.1%).

After removal of most of the water from the bottom phase, a residue of about 14.61 g was obtained which contained 4.7 g sodium sulfate with the remainder being uncharacterized organic material.

The inventive volume ratio of 2:4:1 for pentane:isopropanol:water added in this example gave three distinct phases with most of the desired sodium petroleum sulfonates concentrated in the middle phase with relatively little unsulfonated oil. The bulk of the unsulfonated oil suitable for recycle to the sulfonation process was obtained from the upper pentane-rich phase. The sulfur content of the upper pentane phase was approximately the same as the sulfur content of the vacuum gas oil feedstock indicating that essentially none of the petroleum sulfonates were transferred into the pentane/unsulfonated oil phase during reaction mixture work-up.

EXAMPLE II

A 600 g sample of North Burbank Unit topped crude oil containing 18 weight percent aromatic compounds and 2490 ml of methylene chloride was charged to a 5-liter 3-necked round-bottomed flask equipped with a Y-adapter tube, water-cooled reflux condenser, thermometer, air-powered stirrer, and glass tubing for the introduction of sulfur trioxide.

In a manner similar to that described in Example I, approximately 29.4 ml (56.45 g, 0.7 mol) of $SO_3$ was vapor-transferred into the stirred reaction mixture of $CH_2Cl_2$ and topped crude oil over a period of 4.25 hours and the resulting mixture was stirred an additional hour after all of the $SO_3$ had been added. The reaction mass was treated with approximately 112 ml of 20 weight percent aqueous sodium hydroxide solution to neutralize the sulfonic acids and adjust the pH into the range of 8-9. Methylene chloride was stripped at reduced pressure and to the residual material was added 600 ml pentane, 1200 ml isopropanol and 300 ml water to give rise to three distinct phases (Volume Ratio 2:4:1 for pentane:isopropanol:water; 0.5 ml $H_2O$/g feedstock). This was done at room temperature.

The separated top phase was stripped of pentane leaving a residue of about 406 g of unsulfonated oil suitable for recycle to the sulfonation process which corresponds to about 67.7 weight percent of the 600 g of topped crude oil charged to the reactor.

After stripping the middle phase on a rotary evaporator to remove most of the isopropanol, a fluid residue of 292.8 g was obtained. A 20 g sample of this phase was subjected to an azeotropic distillation with toluene to give 5 ml water (25 weight percent $H_2O$). The remaining sample of the organic phase was dissolved in chloroform and characterized by silica gel elution column chromatography to establish the presence of 3.74 g of unsulfonated oil (18.7%) and 10.74 g of sodium petroleum sulfonates (53.7%). Thus, the principal components in the 292.8 g stripped middle phase were sodium petroleum sulfonates 157.2 g (53.7%), water 73.2 g (25%) and unsulfonated oil 54.8 g (18.7%).

After removal of essentially all of the water from the bottom phase, a residue of about 35.1 g was obtained which contained 12.46 g sodium sulfate with the remainder being uncharacterized organic material.

As noted in Example I, the treatment of the neutralized reaction mass with the inventive volume ratio of pentane, isopropanol and water caused the bulk of unsulfonated oil to be located in the upper pentane-rich phase and the sodium petroleum sulfonates to be concentrated in the aqueous isopropanol middle phase with relatively smaller amounts of unsulfonated oil. It was noted also that the sulfur content of the pentane phase was about the same as the sulfur content of the topped crude oil feedstock indicating that essentially none of the petroleum sulfonates passed into the unsulfonated oil phase during reaction mixture work-up.

EXAMPLE III

Two additional sulfonation treatments with liquid $SO_3$ on a vacuum gas oil feedstock were carried out in essentially the same manner as described in Examples I and II. After neutralization with aqueous sodium hydroxide and stripping methylene chloride, the residual liquids from the two runs were divided into approximately equal portions and worked-up, respectively, as control run (A-1), invention run (B-1), control run (A'-1) and invention run (B'-1). The results of these runs are summarized in Table I to show that the inventive runs (B-1) and (B'-1) were, respectively, more efficient than control runs (A-1) and (A'-1) in regard to concentrating sodium petroleum sulfonates in the alcohol phase: Note the relatively greater amounts of residue and total sulfonate (meq.) in the residues from the stripped alcohol phases in said inventive runs.

TABLE I

Relative Amounts of Sodium Petroleum Sulfonates In Residues From Stripped Alcohol Phases

| Reference | g Residue From Stripped Alcohol Phase | Meq. of Sulfonate* Per g of Residue | Total Meq. Sulfonate In Residue From Stripped Alcohol Phase |
|---|---|---|---|
| (A-1) (Control)[a] | 25.1 | 1.42 | 35.6 |
| (B-1) (Invention)[b] | 46.0 | 1.56 | 71.8 |
| (A'-1) (Control)[c] | 30.9 | 1.59 | 49.1 |
| (B'-1) (Invention)[d] | 42.0 | 1.54 | 64.7 |

*Based on Hyamine 1622 (trademark, Rohm and Haas) titration results (ASTM D1681-62)
[a]Isopropanol alone was added to the neutralized reaction mass remaining after the methylene chloride diluent was stripped. A two phase system resulted comprising an alcohol phase and an oil phase. The phases were separated and the alcohol phase was stripped to a 25.1 g residue.
[b]Pentane, isopropanol and water was added to the neutralized reaction mass remaining after the methylene chloride diluent was stripped. A three phase system resulted comprising a pentane-unsulfonated oil phase, an alcohol-rich phase and a brine phase. The phases were separated and the alcohol phase was stripped to a 46.0 g residue.
[c]Isopropanol and water were added to the netrualized reaction mass remaining after the methylene chloride diluent was stripped. A two phase resulted comprising an alcohol phase and an oil phase. The phases were separated and the alcohol phase was stripped to a 30.9 g residue.
[d]Work-up essentially the same as (B-1) and the separated alcohol phase was stripped to a 42.0 g residue.

The results of this example truly demonstrate that utilizing the three ingredient separating agent in accordance with this invention results in a significantly higher recovery of the petroleum sulfonates than achieved by utilizing either only the alcohol or alcohol and water. This result appears both advantageous and unexpected.

EXAMPLE IV

The sodium petroleum sulfonates prepared in Examples I and II proved to be effective for oil recovery in Berea cores as shown by the results given below. The core runs were carried out essentially in the same manner as described in U.S. Pat. No. 4,125,156.

The oil displacement tests utilized 7.5 percent pore volume surfactant slugs containing 3.6 active weight percent sulfonate and 3.0 weight percent isobutanol in sodium chloride solution of a selected salinity. Surfactant slugs were injected at a frontal velocity of 0.8 ft per day and were preceded by 0.5 pore volume preflush of said selected salinity and were followed by 1.0 pore volume mobility buffer of 1500 ppm polyacrylamide.

The oil displacement tests were conducted in 3 foot long by 3 inch diameter water-wet Berea sandstone cores containing North Burbank Unit oil in a waterflood residual state. In each test the epoxy-encapsulated Berea core was saturated with brine of a selected salinity, followed by an oil flood and finally waterflooded with said brine to residual oil saturation.

The tertiary oil recovery results are given in Table I.

TABLE I

Tertiary Oil Recoveries With Petroleum Sulfonates Derived From Vacuum Gas Oil and Topped Crude Oil

| Run No. | Surfactant Source | Preflush NaCl (wt. %) | % Tertiary Oil Recovered |
|---|---|---|---|
| 1 | Example I | 1.6 | 83.9 |
| 2 | Example II | 1.7 | 80.4 |

The results of this example demonstrate the use and effectiveness of the petroleum sulfonates made and recovered in accordance with this invention.

Reasonable variations and modifications which are apparent to those skilled in the art can be made in this invention without departing from the spirit and scope thereof.

I claim:

1. In a process for producing petroleum sulfonates comprising
   (a) sulfonating a hydrocarbon oil feedstock by contacting said feedstock with a sulfonating agent under sulfonating conditions to obtain a sulfonated product,
   (b) neutralizing said sulfonated product by contacting it with a basic neutralizing agent to obtain a neutralized product,
   (c) contacting said neutralized product with a separating agent comprising alcohol and water to form a separation mixture,
   (d) having the separation mixture separate into
      a top phase
      an intermediate phase and
      a bottom phase, and
   (e) recovering a petroleum sulfonate product from said intermediate phase
   the improvement comprising using as said separating agent in step (c) one that comprises in addition to water and a lower alcohol a lower alkane selected from the alkanes and cycloalkanes having 5 to 10 carbons and mixtures thereof.

2. A process in accordance with claim 1 wherein said sulfonating is carried out by contacting said hydrocarbon oil with $SO_3$ in the presence of a halohydrocarbon diluent and wherein said halohydrocarbon diluent is removed prior to contacting said neutralized product with said separating agent.

3. The process of claim 1 wherein said halohydrocarbon diluent is methylene chloride.

4. A process in accordance with claim 1 wherein the volume ratio of lower alkane:alkanol:water used is in the range of 6:6:1 to 0.25:2:3.

5. The process of claim 1 wherein said separating agent is used in such a quantity that about 0.25 ml to 2 ml of water in said separating agent is employed per gram of hydrocarbon oil.

6. The process of claim 1 wherein said alkanol is an alkanol or a mixture of alkanols having 1 to 4 carbon atoms.

7. The process of claim 1 wherein said separating agent comprises pentane, isopropanol and water.

8. The process of claim 7 wherein the volume ratio of pentane:isopropanol:water is approximately 2:4:1.

9. The process of claim 1 wherein steps (c) and (d) are carried out at ambient temperature.

* * * * *